United States Patent [19]
Heagle et al.

[11] Patent Number: 5,454,946
[45] Date of Patent: * Oct. 3, 1995

[54] FILTER MATERIAL FOR FILTERING LEUCOCYTES FROM BLOOD

[75] Inventors: David G. Heagle, Troutman; John J. Hiers, Elkin, both of N.C.

[73] Assignee: Lydall, Inc., Manchester, Conn.

[ * ] Notice: The portion of the term of this patent subsequent to Mar. 1, 2011 has been disclaimed.

[21] Appl. No.: 199,662

[22] Filed: Feb. 22, 1994

Related U.S. Application Data

[63] Continuation-in-part of Ser. No. 22,642, Feb. 25, 1993, Pat. No. 5,290,449, which is a continuation-in-part of Ser. No. 733,613, Jul. 22, 1991, Pat. No. 5,190,657.

[51] Int. Cl.$^6$ .......................... B01D 39/02; B01D 39/04; B01D 39/06; B01D 39/08
[52] U.S. Cl. .......................... 210/503; 210/504; 210/505; 210/508; 210/509; 428/283; 428/285; 428/286; 428/287; 428/323; 428/327
[58] Field of Search .......................... 210/490, 491, 210/504, 505, 508, 509; 428/283, 284, 285, 286, 287, 288, 323, 327; 422/101; 264/122; 162/109

[56] References Cited

U.S. PATENT DOCUMENTS

| | | | |
|---|---|---|---|
| 4,274,914 | 6/1981 | Keith et al. | 162/109 |
| 4,889,764 | 12/1989 | Chenoweth et al. | 428/283 |
| 4,904,343 | 2/1990 | Giglia et al. | 162/145 |
| 5,190,657 | 3/1993 | Heagle et al. | 210/645 |
| 5,290,449 | 3/1994 | Heagle et al. | 210/503 |

*Primary Examiner*—John Kim
*Attorney, Agent, or Firm*—Griffin, Butler, Whisenhunt & Kurtossy

[57] ABSTRACT

A filter material for filtering leucocytes from a fraction of or whole human blood, comprises a web having a thickness of at least about 1 millimeter and a bulk density of about 0.05 to 0.4 g/cm$^3$. The web has a plurality of interlocked matrix fibers distributed in the web to form a matrix thereof with spaces between adjacent interstices of interlocked fibers. The matrix fibers are composed mainly of about 1 to 3 micron diameter glass fibers, i.e. at least 75% of the weight of the web being the glass fibers. A plurality of fibrillated particles of textile fiber material, having a surface area of between 5 and 100 square meters per gram are disposed within the spaces of the matrix. The weight ratio of the fibrillated particles to the matrix fibers is between about 1:99 and 40:60. A thermoplastic binder is disposed at least at cross-over portions of the matrix fibers, with the amount of the binder being about 0.1% to 10% by weight of the web.

20 Claims, 2 Drawing Sheets

FILTER MATERIAL FOR FILTERING LEUCOCYTES FROM BLOOD

This application is a continuation-in-part of prior U.S. application Ser. No. 08/022,642, filed on Feb. 25, 1993, now U.S. Pat. No. 5,290,449, which in turn is a continuation-in-part of prior U.S. application Ser. No. 07/733,613, filed on Jul. 22, 1991, now U.S. Pat. No. 5,190,657, the entire disclosures of which are incorporated herein by reference and relied upon for disclosure.

BACKGROUND OF THE INVENTION

The prior patent discloses a blood filter and method of filtration for removal of leucocytes from whole blood or blood fractions. The filter material is a shape-sustaining laid textile fiber web having a thickness of at least about 1 millimeter and a bulk density of between about 0.05 and 0.4 g/cm$^3$. The web has a plurality of interlocked, textile fibers which are substantially uniformly distributed in the web so as to form a matrix of the fibers with spaces between interstices of interlocked fibers. Within those spaces are disposed a plurality of fibrillated particles of polymeric material having a plurality of fine fibrils which are interlocked with the adjacent textile matrix fibers such that the fibrillated particles are not substantially displaceable from the web during filtration of blood, and the textile matrix fibers form a support for the web and the fibrillated particles.

As disclosed in that prior patent, for efficient and effective depletion of leucocytes from blood passing through the filter material, both the fiber geometry and the surface area of the fibers are important, and that, very importantly, the surface area must be significantly greater than the usual prior art blood filters, since otherwise the degree of leucocyte depletion (removal) is not sufficient. Further, since fiber geometry and surface area are important for leucocyte depletion, the depth (thickness) of the filter material is also important. Somewhat similarly, since the bulk density of the filter material and the denier of fibers affects fiber geometry and surface area, these are also important.

However, to achieve the high surface area of the filter material required for effective leucocyte removal from blood, a critical component is that of the very high surface area fibrillated particles in the filter material. Ordinary textile fibers cannot provide such high surface areas to the filter material which surface area is required for high leucocyte removal. The fibrillated particles are somewhat elongated particles with an elongated central portion from which radiate a large number of very fine fibrils.

As can be appreciated, it is important to ensure that the small fibrillated particles are not significantly displaced from the filter material during filtration of blood, and, as disclosed in that prior patent, this is achieved by interlocking the fibrils of the fibrillated particles with adjacent textile matrix fibers. Further, especially at higher weight ratios of fibrillated particles to textile matrix fibers, e.g. 6:94 to 10:90, permanent securing of the fibrillated particles in the filter material may be improved by use of means for adhering the textile matrix fibers and fibrillated particles to each other, such as by tackifying adhesives and especially the use of sheath/core fibers for at least part of the textile matrix fibers, e.g. a sheath of low melt temperature polymer and a core of higher melt temperature polymer. When the textile matrix fibers are at least in part such sheath/core fibers, during usual processing of the filter material web, including heating thereof, the sheath softens and causes bonding, upon cooling, between the textile matrix fibers themselves and fibrillated particles, especially the fibrils thereof.

While the filter materials of that prior patent are quite effective for leucocyte removal from blood or blood fractions, the above-noted prior application discloses that the overall performance of those filter materials may be improved in that the efficiency of the filter material (percent leucocyte removal per unit thickness of filter material) can be increased. This means that for a targeted leucocyte removal percentage, the improved filter material of the prior application can be of less thickness than the filter material of the prior patent. This, in turn, means that the amount of blood or blood fractions retained in the filter material of the prior application, after filtration is completed, is less than that of the filter material of the prior patent. While this difference in the amount of retained blood is not an absolute large amount, the difference can be quite important, especially in certain filtrations of blood.

Further, with the filter material of the prior application, less fibers are released from the filter during an AAMI test than with the filter materials of the prior patent.

In regard to the prior application, it was found that if the average sizes (diameter and length) of the matrix fibers are, generally speaking, less than the average sizes of the matrix fibers of the prior patent, increased efficiency of the filter material occurs. It was also found that this is especially true when the matrix fibers are, at least in part, made of certain inorganic materials, especially glass. These smaller matrix fibers could nonetheless be adequately interlock with the fibrillated particles to prevent displacement of either the matrix fibers or fibrillated particles from the filter material during blood filtration when the filter material has therein an added thermo-softening binder.

With such binders, fibrillated particles of larger surface area may also be used and the efficiency of the filter material (and hence the required thickness of the filter material for a targeted leucocyte removal) could further be reduced.

The prior application discloses that the textile matrix fibers of the prior patent may be replaced, at least in part, by the smaller diameter glass matrix fibers when the glass fibers have a diameter between about 0.1 and 5 microns, and especially when the diameter is between about 0.5 and 1 micron, most preferably about 0.65 micron. Example 2 of that prior application shows a 99.9% reduction in leucocytes when the filter material uses 85% of 0.65 micron diameter glass fibers, and the blood being filtered is a usual concentration of blood cells. However, it has been found that, when the concentration of blood cells in the blood to be filtered is increased to higher levels, that percent reduction in leucocyte content of the filtered blood very significantly drops.

Thus, while the filter of the prior application is most satisfactory for the more usual blood filtrations, it is not entirely satisfactory for a wider range of blood filtrations, especially in regard to blood having higher concentrations of blood cells.

It would, therefore, be of substantial advantage to the art to provide an improved filter which can achieve high percentage of leucocyte depletion over a wide range of blood filtrations, especially when the blood filtration involves higher levels of blood cells.

SUMMARY OF THE INVENTION

The present invention provides a blood filter which can achieve very high percentages of leucocyte depletion over a wide range of blood filtrations, including high levels of blood cells. The invention is based on several primary and several subsidiary discoveries.

First of all in this regard, as a primary discovery, it was found that the efficiency of the filter, which allows high leucocyte depletion with a wide range of blood filtrations, is increased with increasing percentages of glass fibers in a web forming the filter. By replacing all or most of the textile matrix fibers of the prior application web with glass fibers, the filter efficiency can be substantially increased. Thus, for such increased filter efficiency, at least 75% by weight of the web must be the glass fibers.

However, as a subsidiary discovery, it was found that at such higher percentages of glass matrix fibers, while the filter efficiency is substantially increased, the amount of fibers displaced from the filter and into the filtered blood increases, and the results of the American Association of Medical Instrumentation (AAMI) standard test, as described in Example 3 of the prior application, were not as low as desired and as shown by that Example 3 of the prior application for lower contents of glass fibers.

As a primary discovery, it was found that not only could the filter efficiency be increased, but the amount of fiber displaced from the filter could be decreased when the average diameter of the glass matrix fibers is increased from that recommended in the prior application. Thus, the average diameter must be between about 1.0 and 3 microns.

As a primary discovery, it was found that, with these larger diameter glass matrix fibers, the filter could achieve the higher efficiency even when the filter contained no, or very reduced amounts of, textile matrix fibers, and only acceptable amounts of fibers are displaced into filtered blood.

As a subsidiary discovery in the foregoing regard, it was found that when the filter contained no, or very reduced amounts of, textile matrix fibers, nonetheless, the filter had very low amounts of displaced fibers during blood filtration, when the filter contains small amounts of the sheath/core fibers described in the prior application and the binder described in the prior application.

Thus, briefly stated, the present invention provides a filter material for filtering leucocytes from a fraction of or whole blood, comprising a shape-sustaining laid web having a thickness of at least 1 millimeter and a bulk density of between about 0.05 and 0.4 g/cm$^3$, the web having: (i) a plurality of interlocked, matrix fibers substantially uniformly distributed in said web so as to form a matrix of the fibers with spaces between adjacent interstices of the interlocked fibers, and the matrix fibers contain at least 75% by weight of the web of glass matrix fibers having an average diameter of between about 1 and 3 microns; (ii) a plurality of fibrillated particles of polymeric material having fibrils and having a surface area of at least 5 square meters per gram substantially disposed within said spaces and the weight ratio of the fibrillated particles to the matrix fibers is between about 1:99 to 40:60; and (iii) a thermoplastic binder disposed at least at cross-over positions of the matrix fibers, the amount of the binder being about 0.1% to 10% by weight of the web. Very preferably, the web also contains up to 20% sheath/core fibers, as matrix fibers, but the sheath/core fibers are not required.

DETAILED DESCRIPTION OF EMBODIMENTS OF THE INVENTION

Figure 1:
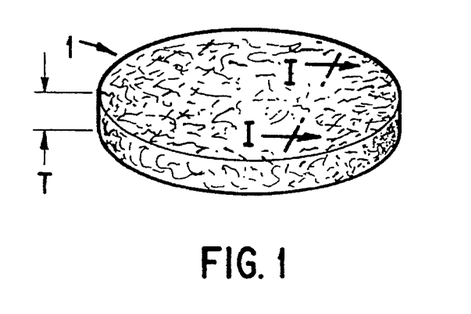
FIG. 1 is a perspective view of the filter made of the present material, in a configuration useful for placing in a filter carrier.

The present invention provides a filter material for filtering leucocytes from a fraction of or whole human blood. FIG. 1 shows such a filter made of such material. That filter, generally 1, is made from a filter material which is a shape-sustaining laid web. As shown in FIG. 1, the web has been cut in a circular configuration to form the filter, and the filter is suitable for loading into a cylindrical filter carrier. In this regard, the term "laid" is used in its ordinary technical sense. Thus, the web must be either air laid or wet laid, as opposed to, for example, needled, since it is in the laying process that the fibers, especially the glass fibers, and the fibrillated particles, so interlock that the glass fibers and fibrillated particles are bound into the filter material such that there is little displacement thereof during filtration. Needled materials, for example, cannot provide such interlocking of the glass fibers and fibrillated particles, and it is, therefore, necessary that the web be a laid web.

The thickness T of that web should be at least 1 millimeter, most preferably at least 2 millimeters, and may be up to about 30 millimeters, or more. A filter depth, as opposed to a web depth, results from placing layers of filter webs one upon another, until the desired filter depth is achieved. Thus, if a filter depth of, e.g., 12 millimeters, is desired and the web has a depth of 2 millimeters, six such layers of web will be required. Thus, rather than producing thick webs which are more difficult to produce, thinner, more easily produced webs are preferred, with an appropriate number of layers of web to achieve the desired filter thickness.

For effective leucocyte depletion of a blood fraction or whole blood passing through the filter, there must be sufficient depth of the filter that the leucocytes have an opportunity to be significantly retained within the filter, both by the geometry and the surface area of the matrix fibers and fibrillated particles. In this regard, a 1 millimeter filter depth (1 millimeter thickness of the filter web) is considered to be the about the minimum effective depth. If the depth of the filter is about 2 millimeters, then a significant increase in leucocyte depletion is achieved, and when the depth of the filter is about 6 millimeters, the depletion of the leucocytes is very substantially increased. However, at about 15 millimeters depth, the pressure drop through the filter when filtering blood begins to significantly increase. That increase in pressure drop continues as the filter depth increases and the pressure drop becomes greater than that which would be desired for ordinary filtration of blood with filter depths above about 20 millimeters. It is for these reasons that the filter depth is usually between about 2 and 20 millimeters, although greater than 20 millimeters and up to about 30 millimeters may be used in special cases where the pressure drop is not of concern. Filter depth is also important in regard to percentage of leucocyte depletion as a function of blood throughput. For example, if the thickness is too small, the filter may start with, for example, a 90% depletion for the first 200 mls of blood, but drop to 80% depletion for the next 200 mls of blood.

The overall bulk density of the filter material must be between about 0.05 and 0.4 g/cm$^3$. As can be appreciated, the density of the filter material relates to the fiber geometry, and the fiber geometry plays an important role in the depletion of leucocytes, in ensuring that the fibrillated particles are firmly and securely locked in the filter material and in ensuring that there is adequate support for the web that - 5 the web will not substantially compact during filtration. This density is the density of the laid web (on a dry basis) but before any binder is added thereto, and also does not include fillers or the like or any purposeful compression of the web other than as described below. At densities significantly below 0.05, the amount of fibers in the filter material is simply not sufficient to ensure a large number of interstices between the fibers for securely locking the fibrillated particles into the filter material and for providing the necessary support for the web. At a density above about 0.4, the amount of fibers to ensure such locking of and support for the fibrillated particles has been exceeded, and the additional density simply results in increased pressure drop, without any significant further benefit to the filter material. Therefore, the density of the laid web must be between about 0.05 and 0.4 g/cm$^3$.

As can be easily appreciated, the density of a laid web of fibers depends on the method of measuring that density, since a thickness measurement must be made to calculate density and the thickness is open to interpretation. Ordinarily, with textile webs, the thickness is measured after a weight is placed on the web to provide a clear upper edge. This weight can vary with the particular filter material, and it is only necessary to have sufficient weight to provide a clear upper edge, but generally a weight of between about 0.5 to 1 lb. per square inch will provide such a clear upper edge.

Figure 2:
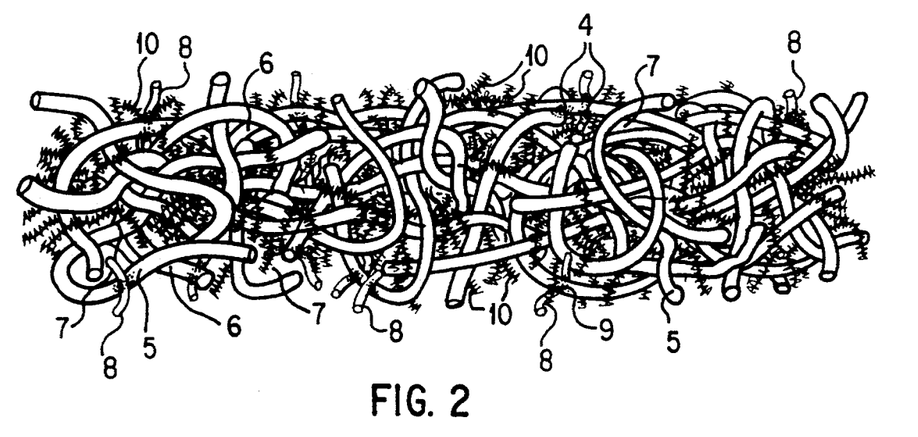
FIG. 2 is a highly diagrammatic partial cross-sectional view of a portion of the filter of FIG. 1, taken along lines I—I.

As seen in FIG. 2, which is a highly diagrammatic illustration of a portion of a section of the filter 1 of FIG. 1, the filter material is comprised of a plurality of matrix fibers 5. In this regard, the present filter material provides high leucocyte depletion because the matrix fibers provide support for the web and prevents substantial compaction of the web during filtration so as to keep the fibrillated particles separated sufficiently that the high surface area thereof is not obscured or reduced due to coalescing or compacting.

The average diameter of the matrix fibers could result from a mixture of very low diameter and short fibers 8 and larger diameter and longer fibers 5. However, when the diameter of these fibers greatly varies, the resulting average diameter therebetween will not provide the interstices required for locking the fibrillated particles and will not provide the necessary support for the web. Neither would this average diameter achieve the fiber geometry described above. Accordingly, to provide an acceptable average length and average diameter, at least 60% of the glass matrix fibers will have lengths and diameters within about 0.3 to 6 millimeters and about 1.0 to 3 microns diameter, and preferably at least 70% and more preferably at least 80 to 85% will be within these ranges.

As noted above, it is necessary to ensure that the matrix fibers are substantially uniformly distributed in the web, so that, correspondingly, the interstices are uniformly distributed and uniformly lock the fibrillated particles in the filter material in a web supported manner. In this regard, the matrix fibers must be so interlocked together that the matrix fibers and fibrillated particles are, in turn, so interlocked that the filter material can withstand a filtering blood pressure drop of at least two feet of head without substantial displacement of the matrix fibers or fibrillated particles from the web or substantially compacting the web.

As can be seen in FIG. 2, the matrix fibers 5 are substantially uniformly distributed through the web so that as to form a matrix of the fibers. That matrix has spaces 7 between adjacent interstices 6 of the interlocked matrix fibers 5. Within these spaces, there are a plurality of fibrillated particles 10 of very high surface area, including the surface area of the fibrils 11 of the fibrillated particles 10 (see FIG. 3). Those fibrillated particles 10 are disposed within spaces 7, as well as along and among the matrix fibers 5, so as to provide the high overall fiber surface area of the filter material. In this regard, fiber surface area refers to the area of the surface of all of the matrix fibers 5 and the fibrillated particles 10, including the fibrils 11 thereof, within the filter material.

As a bench mark, conventional filters, even with very fine textile fibers, may have a total surface area of all fibers of perhaps 0.5 square meters or even perhaps about up to one square meter per gram, although, usually, the total surface area will be much less. Even with non-textile fibers, such as meltblown fibers used in prior art filters, surface areas of only about one square meter per gram can be obtained. In contrast, the total surface area of all fibers and fibrillated particles in the present invention will be at least one and one-half times that surface area and more usually at least two to three or four or five times that surface area, e.g. a total surface area of at least about 1½ square meters per gram.

Figure 3:
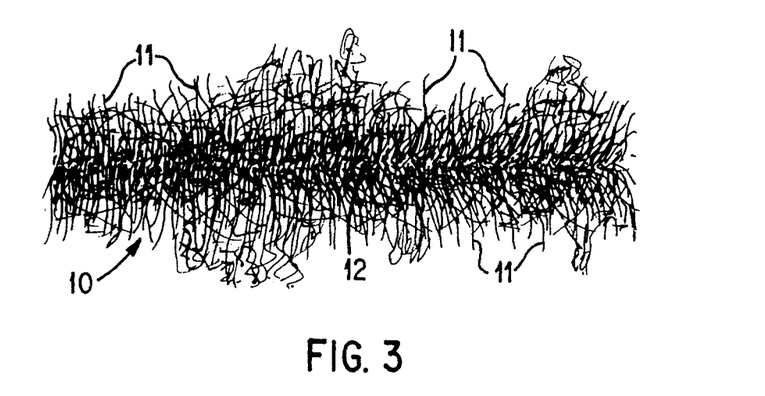
FIG. 3 is a highly diagrammatic illustration of a portion of the fibrillated particle of textile fiber material, used in the present invention.

As highly diagrammatically shown in FIG. 3, the fibrillated particles 10 have a plurality of fine fibrils 11 which extend and radiate from some generally elongated central portion 12 of the fibrillated particles 10. Those fibrils, as diagrammatically shown in FIG. 2, interlock among the matrix fibers 5, and particularly in the interstices 6 between the fibers. Thus, by wrapping the fibrils 11 around the matrix fibers 5, and especially by the fibrils 11 being interlocked between matrix fibers 5 at interstices 6 thereof, the fibrils 11 are securely interlocked with the matrix fibers 5.

A length, width and depth of such a fibrillated particle is, quite apparently, difficult to accurately measure or specify, but for understanding purposes, fibrillated particles have a general overall length of less than 1000 microns, e.g. 5 to 300 microns, but more usually somewhere about 5 to 50 microns. The width and depth vary considerably along the length of the central portion 12 and vary from 0.1 micron or below to 50 microns, but, generally, the widths and depths are between about 0.1 and 5 microns, and more usually between 0.2 and 0.7 micron.

From the above dimensions, it will be appreciated that a particular fibrillated particle 10, as shown in FIG. 2, can be so long that it actually weaves in and out of spaces 7 and one fibrillated particle may serpentinely lie in a number of spaces 7, e.g. up to 100 of such spaces 7. Thus, such a fibrillated particle, and especially the fibrils 11 thereof, has a multitude of interstices 6 with which to interlock.

On the other hand, from the above dimensions, it will be appreciated that a particular fibrillated particle may essentially lie within a single space 7 bounded by adjacent interstices, with the fibrils 11 wrapped around adjacent matrix fibers and locked between adjacent matrix fibers forming adjacent interstices. Also, a particular fibrillated particle may be of any intermediate size between the two sizes discussed above, and combinations of such locking of the fibrillated particles will occur.

The weight ratio of the fibrillated particles to the matrix fibers must be between about 1:99 and 40:60, and especially between about 5:95 and 40:60, and preferably less than about 20:80. If that ratio is less than about 3:97, the additional surface area supplied by the fibrillated particles is marginal for desired leucocyte filtration, and at below about 1:99, the surface area is simply not sufficient to achieve a minimum desired depletion of leucocytes, i.e. at least a 70% depletion. With increasing ratios of fibrillated particles to matrix fibers, the depletion of leucocytes from blood will be correspondingly increased, such that at a ratio of about 5:95, the depletion percentage will be close to about 90%, and at about 10:90, the depletion may be as high as about 99%, for some modes of blood filtration. However, with increasing ratios, it will be appreciated that the number of matrix fibers, and the interstices formed thereby, will be correspondingly decreased, and there may not sufficient matrix fibers to form a support for the web and to keep the fibrillated particles separated. Therefore, higher percentages of fibrillated particles results in lower average pore size and increased flow resistance without any increase in leucocyte depletion. Further, at a ratio of about 40:60, the number of matrix fibers in the filter material is decreased to the point where it is no longer reliable that most of the fibrillated particles will be separated, i.e. the support achieved by the matrix fiber may be insufficient to prevent substantial compacting of the web during filtration, and it is for this reason that the ratio of fibrillated particles to matrix fibers should not exceed about 40:60, particularly should not exceed about 30:70, especially should not exceed 20:80.

The glass matrix fibers 5, as noted above, should have an average diameter of between about 1.0 and 3 microns. These are, of course, very fine non-textile, glass matrix fibers. Preferably, the average diameter will be between about 1.0 and 2.5 microns and especially between about 1.5 and 2.0 microns, e.g. about 1.8 microns.

In the above regard, it will be noted that the diameters of the present glass matrix fibers are different from the diameter of the glass fibers used in the prior application. In the prior application, it is disclosed that the glass fibers used in the web of that prior application can range anywhere from 0.1 micron to 5 microns, with preferred ranges between 0.5 and 1 micron, and in Example 2 of the prior application, the diameter of the glass fibers actually used was 0.65 micron. These ranges of diameters are quite satisfactory when the web contains a significant amount of textile matrix fibers, but it has now been found that these ranges of diameters are not satisfactory when the web contains smaller amounts or no amounts of textile matrix fibers.

In this latter regard, it has been found that the average diameter of the present glass matrix fibers when used in the present percentages must be at least 1 micron, as opposed to the preferred diameter of about 0.65 micron of the prior application. Below 1 micron, and in the present absence or substantial absence of the larger textile matrix fibers, the resulting web is liable to unduly compact and substantially adversely decrease filtration. This is because, with substantial compacting, the spaces 7 decrease and fibrillated particles in adjacent spaces 7 can contact each other in such a manner as to obscure the filtration function of the contacted fibrillated particles. Thus, the present glass matrix fibers must provide sufficient support to the web to prevent such compacting and decease in spaces 7. Above about 3 microns, the overall filtration of the web begins to considerably decrease due to the decrease in the number and surface area of the glass fibers. Indeed, preferably, the average diameter of the present glass matrix fibers is between about 1.0 micron and 2.5 microns, for the same reason, which is a relatively narrow range.

This considerably more critical and narrow range for the present glass matrix fibers is a result of the absence or substantial absence of the textile matrix fibers of the prior art application, and the absence or substantial absence of the function those textile matrix fibers performed. In this regard, in the prior application, the textile matrix fibers performed relatively little filtration function in view of the relatively large diameters thereof, e.g. in the order of several or more orders of magnitude larger diameters than the diameters of the glass fibers. As noted above, the function of the textile matrix fibers is that of providing a support structure and to lock the fibrillated particles into the web, which particles provided the major filtration function.

Without these textile matrix fibers or with a very reduced amount thereof, the support structure provided by those textile matrix fibers is no longer present or greatly reduced. Thus, that support must be provided by the present glass matrix fibers in the present web. However, glass matrix fibers below 1 micron in diameter are not sufficiently rigid to provide that support structure, hence allowing undesired compaction of the web during filtration. Also, as noted above, glass matrix fibers having average diameters above about 3 microns begin to decrease the filtration function of the web, since the present smaller diameters of the present glass matrix fibers allow those fibers to perform a significant filtration function, as opposed to the larger diameter of the textile matrix fibers.

Thus, in the present web, with the present high percentage of glass fibers functioning as the matrix fibers, i.e. at least 75% by weight of the web, the average diameters of the glass fibers have been found to be somewhat critical, as opposed to the average diameters of the glass fibers used in the prior application which did not necessarily have to carry out major support and filtration functions. Outside of the present relatively critical range of average diameters for the glass matrix fibers, the support and filtration function of a web will be significantly variable and unpredictable, which is not acceptable to the art.

The above range is also somewhat critical, since to achieve the present improved efficiency of the filter, the glass matrix fibers must be at least 75% by weight of the web. At less than 75%, the filtration efficiency is not significantly increased. Indeed, it is preferred that the glass matrix fibers are 80% of the weight of the web, and even 90%. Indeed, most preferably, all of the matrix fibers are the glass fibers, with the exception of a small amount of sheath/core fibers, as explained below.

The glass of the matrix fibers may be any conventional glass, such as E-glass, S-glass, borosilicate glass, etc. Further, many conventional ceramic fibers have essentially glass-like physical properties, as opposed to mainly ceramic properties. Thus, ceramic fibers (not based on silica) may be used when those ceramic fibers have glass fiber-like physical properties and are, therefore, intended in the definition of glass fibers.

Irrespective of the type of glass, as is well known, glass fibers are, on a relative basis as compared with, for example, polymeric textile fibers, quite stiff. While this stiffness tends to result in a loftier structure and, hence, more depth filtration, this also means that it is difficult to ensure that the stiff glass fibers have been entwined sufficiently to ensure that the matrix fibers are interlocked, especially since current manufactures of these fine glass fibers have considerable differences in the lengths thereof, e.g. the average length of these fibers can be between about 0.3 and 6 millimeters or even outside of these ranges. By selecting the glass fibers, with average diameters between about 1.0 and about 3 microns, the usual average lengths of these fibers are between about 0.5 and 5 millimeters. Especially when selecting glass fibers having an average diameter of about 1.8 microns, the average lengths are more predictably within the above range, i.e. between about 1 and 4 millimeters, and the difficulty of ensuring interlocking with the fibers and fibrillated particles can be mitigated, but it cannot be avoided altogether.

While the use of a relatively small amount of sheath/core matrix fibers, as described more fully below, will mitigate this problem, the problem cannot be altogether avoided thereby. It appears, in this regard, that the thermoplastic, and, hence, heat softenable, sheath, disposed on the textile fiber core is not necessarily capable of fully adhering the much smaller and somewhat mobile glass matrix fibers. The number of these small glass fibers is quite large, and with this large number of relatively stiff, short glass fibers, complete securing by sheath/core matrix fibers is not ensured.

In view of the above, the securing of the glass matrix fibers into the web requires a separate binder in the web. While theoretically this binder could be a thermosetting or thermoplastic binder, thermosetting binders are not fully satisfactory for a number of reasons, including the need for a catalyst which may not be compatible with blood filtering, longer reaction times for cross-linking and, hence, prolonged production times, generally uniform distribution thereof throughout the web instead of being concentrated at critical cross-over positions, as explained below, larger amounts to ensure binding of the glass matrix fibers, and a somewhat stiff and boardy filter material. Hence, the binder must be a thermoplastic binder.

In this latter regard, the binder may be any thermoplastic binder, e.g. a binder having a softening temperature below about 400° F., preferably below 350° F., and especially below about 300° F. or 250° F. or even below 220° F. In this regard, softening temperature is defined as that temperature at which the thermoplastic binder sufficiently softens so as to adhere to both the matrix fibers and the fibrillated particles. However, it was found that certain thermoplastic binders have special advantages, in that the binders either have particularly good adherence to these fibers or tended to migrate to fiber cross-over positions, as explained below, or both.

Suitable thermoplastic binders are polyvinyl acetate, polyvinyl chloride, polyacrylics and acrylates, polyacrylonitrile, polybutadiene, polyethylene, polyisoprene, polyvinyl acetate ethylene, polyvinyl acetate acrylate and polystyrenebutadiene. It is also possible to use desolubilized gums such as polyvinyl alcohol and cellulose gum, but the desolubilized versions of these water-soluble gums are much more difficult to ensure sufficient desolubilization and are therefore not preferred. These binders may be applied to the web prior to or during formation thereof and as powders or solutions, but it has been found that very special advantages are provided when the binders are applied to the already formed web and as an emulsion.

In this regard, as can be seen from FIG. 2, in order to ensure that the matrix fibers 5 are secured together, it is only necessary to have the binder at cross-over positions 9. Any other disposition of the binder will not significantly improve the binding of the fibers and will only serve to decrease the filtration throughput. Thus, if the binder could be arranged to be substantially disposed only at these cross-over positions, securing of the matrix fibers is ensured and a minimum of stiffening binder may be used.

It was found that if the binder, in emulsion form, is applied to the already formed web, the emulsion sized particles of the binder plastic in the emulsion tend to be more removed from the emulsion at these cross-over positions than at other places throughout the web. Thus, the emulsion form of the binder proved to be a substantially superior form thereof. While not bound by theory, as can be seen from FIG. 2, the cross-over positions constitute the closest physical restraints for removing binder particles from the emulsion. Hence, if the emulsion is in effect filtered through the web, the binder particles will be preferentially removed from the emulsion at these cross-over positions and the retained binder particles are, therefore, in the preferred position in the web for maximum binding of the matrix fibers with minimum amounts of binder.

As can be appreciated from the above, this preferred filtering action of the binder particles cannot be reasonably achieved with a solution or melt of the binder, but only from a dispersion of the binder. Further, it could not be achieved when the binder is added before or during forming of the web; it can be achieved only after the web is formed. Also, while a dispersion could function even if not in emulsion form, quite obviously, an emulsion form will provide a more uniform dispersion and deposition at the cross-over positions.

It has also been found that an emulsion form of the binder has another advantage. As described more fully below, after the emulsion is applied to a formed web, the web is dried, usually, by serpentine passage over heated cans. Cans alternately heat the web from one surface thereof and then from the other surface thereof. Due to the alternate heating of those web surfaces, the continuous phase of the emulsion (usually water but other continuous phases such as alcohols could be used) migrates toward those heated and, hence, drier surfaces. This migration of the continuous phase carries free (unattached) binder particles therewith and causes an overall preponderance of the binder particles to attach nearer the surfaces of the drying web. This preponderance of attachment of the binder particles nearer the surfaces of the web very securely locks the matrix fibers nearer the surfaces. This secure locking further ensures that matrix fibers nearer the surface will not be displaced into the blood during filtration thereof, and it is the matrix fibers nearer the surfaces of the web which are more liable to be so displaced.

The emulsion could be applied to the web by conventional padding or printing of the web with the emulsion, or even immersing the web in the emulsion, but it will also be apparent that the above-described desired filtering action of the binder particles is far more sure when the emulsion is applied to only one side of the web, e.g. by spraying one side of the web, e.g. top side, with the emulsion and with a reduced pressure on the other side of the web. This means of applying the emulsion is also most convenient for use in a conventional web-forming process and apparatus, as discussed more fully below.

In view of the above, certain of the above-described polymeric binders are preferred, since they can easily be formed into stable emulsions. Among these are polyvinyl acetates and acrylates, polyacrylics and acrylates, polybutadiene and polyisoprene, with polyacrylics and acrylates being more preferred.

The emulsion may have solids contents between about 0.1% and 50% and still provide the required filtering action of the binder particles, especially between about 0.5% and 20%, e.g. between about 1% or 5% and 10%. This will also produce an add-on of binder particles to the formed web of about 0.1% to 10%, based on the weight of the web. At about 10% add-ons, the adherence of the glass fibers is well ensured and additional add-ons beyond this amount can cause decreases in pore sizes of the filter material, along with decreased throughput and increased pressure drop. Further, below that 10% add-ons, the flexibility of the finished filter material is not substantially reduced, so long as the binder polymer is flexible at room temperature and has a glass transition temperature of above 100° F. At less than about 0.1% add-ons, the amount of binder is insufficient, although add-ons of about 0.25% or 1% or more are quite satisfactory.

Figure 4:
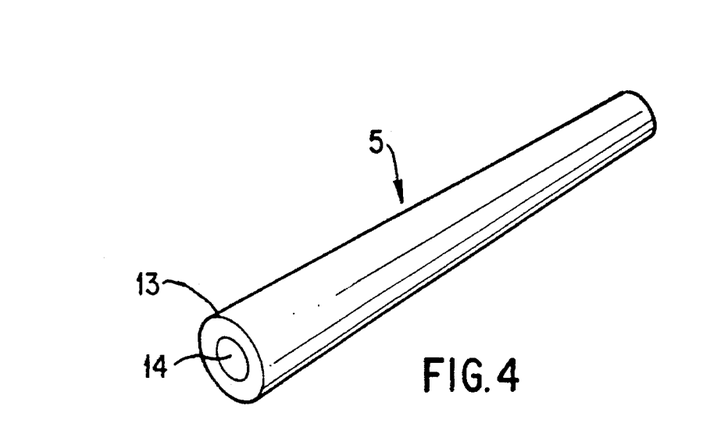
FIG. 4 is a perspective view of a sheath/core fiber useful in the present invention.

A portion of the matrix fibers 5 may be sheath/core organic or inorganic fibers, as noted briefly above, i.e. having a sheath 13 and a core 14 (see FIG. 4). Usually, the sheath 13 will be of a low melt temperature polymer, and the core 14 will be of a higher melt temperature polymer. For example, the core 14 may be a polyester polymer, and the sheath 13 may be a low-melt olefin, such as polyethylene. When a small portion of the matrix fibers of the filter material are the sheath/core fibers, the web of the filter material, when being processed, is subjected to temperatures such that the web has experienced temperatures sufficient to at least soften the polymer sheath 13 and cause at least some adherence of that softened sheath of the matrix fibers 5 and to the fibrils of the fibrillated particles. As can be appreciated, this will cause a bonding of the matrix fibers together, to improve the strength of the interstices, and will cause bonding of the fibrils of the fibrillated particles to the sheath of the sheath/core fibers. This will ensure better locking of the fibrillated particles in the filter material.

While as little as about 1% of the matrix fibers may have the sheath thereon, and at least some improvement will be provided for securing the fibrillated particles in the filter material, generally, at least about 5% of the matrix fibers will be the sheath/core fibers. On the other hand, while a much larger percentage of the matrix fibers could be the sheath/core fibers, this would render the resulting filter material rather stiff, which is not desired, simply for convenience of handling, and, therefore, it is preferred that the sheath/core fibers be no greater than about 30% of the matrix fibers. Thus, a preferred range for the sheath/core textile fibers is between about 5% and 20% of the matrix fibers. Within this range, the filter material so locks the fibrillated particles into the filter material that the filter material can withstand a filtering blood pressure drop of at least five feet of head without substantial displacement of the fibrillated particles from the web.

The sheath/core fibers, if used, may have a denier of about 0.05 to 0.75 denier, but if 30% or less of sheath fibers are used, that denier may be higher, e.g. up to about 3 or 4 denier. For example, when about 5% or 10% sheath/core fibers are used, conventional 2 denier sheath/core fibers may be used.

The sheath/core fiber, if used, may have a core of textile fiber material, and the sheath may be any low melting polymer. While a wide range of low melting polymer sheaths are known to the art, including methacrylates, vinyls and the like, polyolefin polymers, such as polyethylene or polypropylene, are preferred, since those polymers provide sheaths with very low softening points, and it is easy to soften those sheaths to provide the required adherence. The thickness of the sheath is essentially immaterial, since the only requirement of the sheath is that there be a sufficient layer of the sheath for adherence to adjacent fibers and fibrillated particles. Thus, the sheath can be from as little as 1% to 50%, e.g. 5 to 30% or 10 to 20% of the core diameter.

The fibrillated particles are particles of a synthetic or natural polymer, and a wide range of such polymers may be used, since it is not the particular polymer but the surface area thereof which is important. However, the polymers must be capable of substantial fibrillation, for the reasons expressed above. Thus, generally, the polymer will be a textile fiber material, e.g. polymer, since textile fiber materials, usually, are capable of being fibrillated to a high degree. Any of the conventional textile fiber materials may be used as the fibrillated particles. However, it is preferred that the fibrillated particles be particles of the textile fiber materials of polyester fiber material, acrylic fiber material, nylon fiber material, polyolefin fiber material and cellulosic fiber material, since these materials easily fibrillate to high degrees and provide fibrillated particles with a multitude of fibrils, as described above. These materials also provide fibrils which easily attach to and lock with the matrix fibers, with or without sheath/core fibers. Further preferred is where the fibrillated particles are made of a textile fiber material which is predominantly a cellulosic fiber material, since fibrillated particles of that material provide a large number of fibrils, and it is especially preferred that the cellulosic fiber material be cellulose acetate, since a great number of fibrils are produced with that material, and the material has a natural hydrophilic nature and, thus, an affinity for leucocytes.

It is not necessary to describe in detail the fibrillated particles, since these fibrillated particles are known to the art and are commercially available. A full description of such fibrillated particles may be found in U.S. Pat. No. 4,274,914 to Keith, et al, issued on Jun. 23, 1981. That patent describes, in detail, the method of manufacture of the fibrillated particles and the fibrillated particles themselves. Those fibrillated particles have been used in the art as binders, primarily, especially in filter papers, and as especially used for binding adsorbents, such as activated carbon powders, in non-woven media. Among other applications are combustible shell casings, specialty papers, speaker cones, and substitutes for asbestos or aramid fibers in friction materials.

The aforementioned patent also describes applications of the fibrillated particles to cigarette filters and face mask filters, where the fibrillated particles form those filters in combination with various fibers, particularly acetate and polyester fibers. Tobacco smoke filters are particularly described, and the use of the fibrillated particles in forming webs for cigarette-filter purposes is set forth in detail. Accordingly, while a detailed description of the fibrillated particles and the process for producing the present filters need not be set forth in this specification, a brief explanation is set forth below.

Thus, very briefly, those fibrillated particles are three-dimensional particles, and the depth is approximately equal to the width. These particles are not fibers and cannot be spun into a yarn, i.e. are not textile fibers, e.g. of staple length. They may be best diagrammatically visualized as extremely small "duck down", in the sense of their physical appearance as viewed through a microscope. The fibrils of the particles are extremely small, e.g. generally less than 0.01 micron in diameter and in the order of 1 to 50 microns long. The fibrils radiate from an elongated central portion, but not in any organized fashion.

In all of the above, the textile art terms are used in their common senses. Thus, the term "textile fiber material" or the like is used in its common sense, i.e. that the material, e.g. a polymer, is capable of being formed into a fiber which can be processed by conventional textile machines into a textile material, either woven or non-woven. Of course, the present glass matrix fibers are, therefore, not a "textile fiber material" in the sense that the present glass fibers are too small to be formed into, e.g., a yarn, and cannot be formed into a woven textile.

Figure 5:
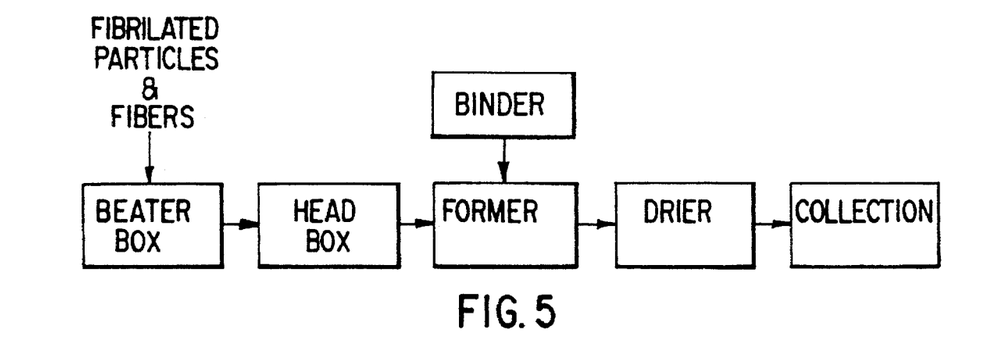
FIG. 5 is a block diagram of the overall preferred process for making the present filter material.

As shown in FIG. 5, the process, which is a known process and generally described in the prior patent, mixes the fibrillated particles, the glass matrix fibers and the sheath/core fibers and/or textile matrix fibers, if either is used, in a beater box to provide a furnish thereof. While the weight percent of fibrillated particles and fibers to the water in the beater box can vary widely, for most applications of fibrillated particles to be incorporated in the fibers, the total solids content (fibrillated particles and fibers) should be somewhere between about one and five percent. Sufficient mixing in the beater box is conducted until a homogenous slurry of the fibers and particles is obtained.

Thereafter, the furnish slurry is fed to a head box of an ordinary paper-making machine. Of course, if desired, intermediate stock tanks and mixers may be used, depending upon the particular machine and the schedule of processing thereon, all of which is well known in the art. Any of the conventional paper-making machines may be used, e.g. a rotating screen machine, a perforated drum machine, and the like, but a usual Fourdrinier machine is preferable, in view of the simplicity of operation of that machine and the control of the web thickness achieved thereby.

In any event, the furnish slurry of fibrillated particles and fibers is fed from the head box to the former of the machine, whether it be the rotating perforated drum or rotating screen or the Fourdrinier machine, and that slurry of fibers and particles is dewatered, by vacuum, to form a wet web.

After the vacuum is applied to the underside of the web, preferably, the vacuum is discontinued and then the binder emulsion is applied to the top side thereof and preferably the vacuum is thereafter reapplied. This application of the binder can be by way of a padding roll or a squeegee bar or doctor blade, but preferably it is simply sprayed onto the web with conventional spray jets, positioned so as to provide a relatively uniform wetting of the top side of the web by the sprayed emulsion. The conventional subsequently applied vacuum to the underside of the web sucks the emulsion into and in part through the web and filters the binder particles therefrom so as to deposit the binder particles predominantly at the cross-over positions, as explained above. No particular degree of vacuum is required, and, indeed, adequate filtering of the binder particles will take place with no vacuum or very high vacuum, e.g. −12 lbs. gauge.

That wet web is then passed to a drier, which is usually a series of steam-heated cans, and is heated sufficiently in a serpentine travel to dry the web and set the binder. In the case of the use of sheath/core fibers, that drying temperature must be sufficient to ensure that the sheath of the sheath/core fibers is sufficiently softened to achieve the bonding, described above. That temperature, of course, will vary with the particular sheath, but, generally speaking, steam-heated cans with steam up to 1 to 2 atmospheres of superheat is more than sufficient to cause such adherence of the usual sheathed fibers, as well as set the binder. If a sheathed fiber is not used, then the steam-heated cans can be at almost any temperature, e.g. 120° F. to 300° F., consistent with setting the binder and drying the web to a relatively low moisture content, e.g. less than 10%, or usually less than 5% or 2% by weight moisture. From there, the dried web is collected in an ordinary collection mechanism, e.g. a roll collecting mechanism, and is then ready for cutting into desired filter shapes.

The setting temperatures for the binder will vary substantially with the particular binder. The setting temperature must be high enough to cause the binder to tackify and adhere to the glass fibers. More preferably, the heat softened binder will be at a temperature high enough to at least partially move or flow to form configured binder pools, as shown in FIG. 2. For most binders, especially the preferred binders, the temperature will be at least 150° F., especially at least 200° F. and as high as 250° to 275° F.

As a means of avoiding any non-wetting and, hence, decreased filtration, in the filter material, the filter material may be treated with a small amount of FDA approved wetting agents, which are known to the art, e.g. the Tweens surface active agents.

Figure 6:
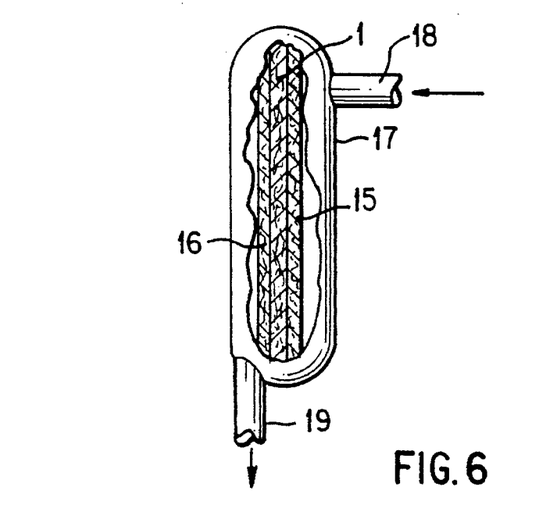
FIG. 6 is a diagrammatic view, partially in broken section, showing a useful, typical, completed filter arrangement, including the filter case.

The filter material may be formed into a filter device in any of the usual manners of the art, and FIG. 6 shows an acceptable example thereof. As shown in FIG. 6, the filter material 1 may be sandwiched between a prefilter 15 and a subsequent filter 16. The prefilter 15 is used to remove large agglomerates and the like which often occur in stored blood, and this prefilter can be any of the usual prefilters known in the art for that purpose. These prefilters can be woven or non-woven textile materials or metal meshes or the like, and the particular prefilter can be chosen as desired.

Similarly, the subsequent filter 16 may be simply a supporting subsequent filter, to give mechanical support to the present filter material and the prefilter. That subsequent filter may be, for example, a woven mesh or a wire mesh, simply to provide support for the pressure drop across the entire filter element (the prefilter, the present filter material and the subsequent filter). Here again, this subsequent filter can be as in the prior art, and no particular details are required in connection therewith.

The filter assembly is held in a conventional housing 17 which has a conventional inlet 18 and a conventional outlet 19. The filter assembly is held in that housing in any convenient manner for mechanically locking the filter element into the housing, e.g. mechanical clamps. Such housing, along with the filter elements therein, is desirably disposable, and with the low cost of the present filter material, such a filter assembly in such a housing is disposable at a low expense.

While FIG. 6 illustrates a convenient and conventional housing and arrangement of the filter elements, any of the other conventional housings and arrangements of filter elements known to the prior art may be used with the present filter material, since the present filter material is amenable to almost any desired configuration.

For certain filtering applications, it is desirable to choose among various properties of the filter material for achieving a desired end result. With the present filter material, choices of properties of filtration are easily obtained. Thus, for example, where the filtration is intended to remove larger particles in the blood, with lower levels of depletion of leucocytes, then the filter material may have a relatively low ratio of fibrillated particles to matrix fibers. On the other hand, where a high depletion of leucocytes is required, but the rate of throughput of the blood through the filter is not particularly critical, then a relatively high ratio of the fibrillated particles to matrix fibers may be used.

Alternatively, such changes in surface area of the filter material may be achieved by choosing the surface area of the fibrillated particles. Thus, one could achieve such a filter material, as described above, by choosing fibrillated particles with a relatively low surface area, e.g. 10 square meters per gram, or, with the same ratio of fibrillated particles to matrix fibers, a filter material of high surface area could be achieved by choosing fibrillated particles with a relatively high surface area, e.g. 30 or 50 or 70 square meters per gram.

A preferred method of achieving different properties of the filter material is that of using fibrillated particles with a relatively high surface area, e.g. between about 10 and 60 or more square meters per gram, and adjusting the ratio of fibrillated particles to matrix fibers. However, with the present glass matrix fibers, fibrillated particles having surface areas up to 100 square meters per gram may be used and still retain those particles in the filter material.

The foregoing methods of selecting filtration properties are applicable to the present filter within the above-noted percentage of glass matrix fibers in the web, i.e. at least 75% or greater. However, especially when the percentage of glass matrix fibers is in the higher ranges of these percentages, the above selection of filtration properties can be easily achieved simply by varying the percentage of glass matrix fibers in the web. This is because, with the present filter material, as opposed to the preferred filter materials of the prior application, the present glass matrix fibers form a substantial filtration function, as opposed to the textile matrix fibers of the prior application.

In this regard, the textile matrix fibers of the prior application have average deniers of between about 0.05 and 0.75, most preferably between 0.2 and 0.5 denier. Thus, the diameter of these textile matrix fibers is relatively large as compared with the diameter of the present glass matrix fibers, e.g. in the order of more than several orders of magnitude greater in diameter. The larger diameter textile matrix fibers are simply too large to achieve any significant filtration of white blood cells in the web densities described in the prior application and function, primarily, for providing a support structure and for locking the fibrillated particles into the web, which particles provide the major filtration properties of the filter of the prior application. Thus, simply changing the percentage of the textile matrix fibers within the parameters described in the prior application will have a relatively small affect on the filtration properties of the resulting web.

However, since the present glass matrix fibers have much smaller diameters, e.g. in the order of more than several orders of magnitude smaller in diameter, the glass matrix fibers perform a very significant filtration function, apart from the filtration function of the fibrillated particles. Therefore, as opposed to the recommended web of the prior application, the filtration function of the present web can be significantly affected by the percentage of the present glass matrix fibers in the present web, and this is a substantial difference between the two webs. This difference is dramatically demonstrated in the below Examples, where the results in Table I show very increased filtration properties achieved by substituting glass matrix fibers for the textile matrix fibers of the prior application, as discussed below.

The invention will now be illustrated by the following examples, where all percentages and parts are by weight, unless otherwise noted, which is the case of the foregoing specification and claims.

EXAMPLE 1

Preparation of Prefilter 3 denier and 6 denier polyester fibers (Dacron Type 54) were carded on separate cards. The carded webs were crossed lapped separately onto a moving conveyor to form a mat with discrete layers of 3 and 6 denier fibers. The mat was needled with a conventional needle-punching machine. The needled mat was hot calendared (350° F.). The 3 denier side of the mat was glazed with a hot (500°–550° F.) knife. This material is Lydall style #CW140 which is a commercial filter material for use in a cardiometry reservoir.

Preparation of Comparison Filter Materials

A wet laid non-woven was produced in the following manner: 75% Teijin 0.5 denier polyethylene terepthalate (PET) fibers of about 6 to 7 millimeters average length, 10% of Code 106 microglass fibers (Schuller—formerly Manville) having an average diameter of about 0.65 microns, an average length of about 3 millimeters, 10% Chisso EKC 2 denier core (polypropylene)/sheath (polyolefin copolymer) fibers of about 5 to 9 millimeters average length and 5% Hoescht-Celanese cellulose acetate "fibrets" (fibrillated particles of textile fiber material) were weighed with adjustments made for the moisture content of the materials. Thus, in this example, most of the matrix fibers are the textile matrix fibers of the prior application, as opposed to the present glass matrix fibers. This furnish was placed in a commercial web-forming machine at about 5% in water. The furnish slurry was stirred at high speed for 2 minutes to achieve good dispersion. This slurry was discharged from the dump box to a moving screen. Dewatering by vacuum (−5 psig) resulted in the forming of a web on top of a screen wire. An acrylic polymer emulsion of about 48% solids (Rohm & Haas HA8) was diluted to about 0.25% solids and sprayed on the top of the dewatered web to wet the web to excess of saturation. Further dewatering was achieved by using the same vacuum. The web was dried at 250° F. on steam-heated cans to produce the present filter material. The thickness of the filter material was approximately 2 millimeters, and the add-ons of binder was about 5%. This filter material is similar to that described in Example 1 of the above-noted prior application.

Testing

Part of the dried web and prefilter were die cut to pieces of about 2.5 inches in diameter and about 3.75 inches in diameter. Selected numbers of the filter material were inserted into a test filter rig similar to that shown in FIG. 6, where the prefilter and filter material are clamped together to form a filter media. The filter media was oriented in the vertical direction and the blood entered at the bottom of the filter media and exited at the top (opposite to that shown in FIG. 6). The media was oriented so that blood first encountered the prefilter material (3.0 denier side first).

The rig was connected with tubing to units of human packed red blood cells about 10 days old. The packed cells were passed through the filter. The results of several similar tests are shown in Table I.

EXAMPLE 2

The same prefilter of Example 1 was used, but the filtering material was made of 80% Type 108B microglass having an average diameter of about 1.8 microns and an average length of about 3 millimeters (Schuller—formerly Manville), 10% of the sheath/core fibers and 10% of the fibrillated particles of Example 1. Otherwise, the filter material, including the binder, and add-ons were the same as in Example 1. Thus, in this filter material most of the matrix fibers are glass fibers, as opposed to most of the matrix fibers being textile fibers as in Example 1. Selected layers of the filter material and a layer of the prefilter were placed in the test rig of Example 1, and the test described therein was carried out. The results of several similar tests are shown in Table I.

As can be seen from Table I, Test No. 1 uses the filter of Example 1 (mostly textile matrix fibers of the prior application) and reduces white blood cells (WBC) from 5700 to 677 (88% leucodepletion), which is an excellent result. However, Test No. 2 uses the filter of Example 2 (mostly glass matrix fibers of the present invention) and reduces the WBC from 5700 to 261 (a 95% leucodepletion) which is a very excellent result.

However, as shown by Tests Nos. 3 and 4, when the white blood cells (WBC) are more concentrated, i.e. 7700 cells/microliter, instead of the 5700 cells/microliter of Tests Nos. 1 and 2, the differences between the filters of Example 1 and Example 2 become unexpectedly pronounced, Thus, in Test No. 3 (with the filter of the prior application), the WBC were reduced only from 7700 to 2800 (64% leucodepletion), while in Test No. 4 (the present filter), the WBC were reduced from 7700 to 17 (a 99.8% leucodepletion), and this is a very surprising result.

Even at intermediate white blood cell concentrations, i.e. 6800 WBC, of Tests Nos. 5 and 6, the foregoing surprising result is shown, in that Test No. 5 (the filter of the prior application) reduced the WBC from 6800 to 1600 (76.5% leucodepletion), while Test No. 6 (the present filter material) reduced the WBC from 6800 to 500 (92.6% leucodepletion). Further, as shown by Tests Nos. 7 and 8, at lower concentrations of white blood cells, the present filter material (Test No. 8) reduced the WBC from 6100 to less than 5.5 (5.5 being the lowest detectable white blood cell concentration of the test—thus, the actual concentration may have been 0), while the filter of the prior application (Test No. 7) reduced the WBC from 6100 to 505.

Thus, with the present invention, at lower concentrations of white blood cells, it is possible to obtain virtually leucocyte-free blood, which is very important to the art for certain uses of the filtered blood.

Tests Nos. 9 and 10 are with 3.75 inches of filter material (provides more cell loading area), and the filter of the prior application (Test No. 9) reduced the WBC from 7300 (a higher concentration) to 200, while the filter of the present invention (Test No. 10) again reduced the WBC from 7300 to less than 5.5 (limit of the test and may be 0), which is, again, virtually leucocyte-free blood.

These results are, indeed, quite impressive, and from Examples 1 and 2 it is seen that these impressive results are achieved by using glass fibers as the major or only matrix fibers in the filter of the prior application.

EXAMPLE 3

In this example, the same prefilter of Example 1 was prepared and the procedure for Preparation of Comparison Filter Materials of Example 1 was followed to produce a comparison filter, except that the comparison filter had 85% of the type 108B microglass fibers, 10% of the sheath/core fibers and 5% of the fibrillated particles. Samples of the comparison filters of Example 1, Example 2 and this Example were die cut to pieces of about 3.75 inches in diameter and tested in the manner described in Example 1. The results of this testing are shown in Table II.

As can be seen from Table II, Test No. 11, which is the same filter material as described in Example 1 (75% PET fibers, 10% sheath/core fibers, 5% fibrillated particles and 10% microglass fibers), reduced the WBC from 10800 to 150 or 98.61% when using the 3.75-inch diameter filter. On the other hand, Test No. 12, which is the same filter material as described in Example 2 (0% PET fibers, 10% sheath/core fibers, 10% fibrillated particles and 80% microglass fibers), reduced the WBC from 10800 to less than 5.5 (which is below the limit of the test method and may be 0), or greater than 99.99% (could be 100%), when using a 3.75-inch diameter filter.

Thus, by substituting the present microglass fibers for the PET fibers, a very significant improvement in leucodepletion is achieved.

Test No. 13, which is the filter material of Example 3, is the same as Test No. 12, except that Test No. 13 has 5% of the fibrillated particles, instead of 10%, and has 85% of microglass fibers, instead of 80%. As can be seen from Table II, thus reducing the fibrillated particles from 10% to 5% and increasing the microglass fibers from 80% to 85% has only a marginal effect, in that Test No. 13 shows the WBC reduced from 10800 to 33.3 or a 99.62% reduction. This Example shows that after a minimum amount of fibrillated particles are in the filter material to achieve the present higher leucocyte depletion, adding additional amounts of fibrillated particles does not significantly increase the leucodepletion. This is understandable, since once a minimum surface area has been provided by the fibrillated particles to adhere and trap the white blood cells, any additional surface area achieved by increased amounts of fibrillated particles serves no substantial amounts of fibrillated particles serves no substantial increased function.

Of course, the minimum amount of fibrillated particles (and, hence, surface area) will depend on the amount of white blood cells to be filtered, the volume of PRBC to be processed, and the diameter of the filter itself. However, within reasonable limits, with the present invention, a wide range of these parameters can easily be tolerated. Note, in this regard, that both Test No. 10 (Table I) and Test No. 12 (Table II), using the same filter material of Example 2, produced greater than 99.99% leucodepletion, even though the WBC to be filtered increased from 7300 (Test No. 10) to 10800 (Test No. 12).

Having described the invention, it will be apparent to those skilled in the art that the specific embodiments discussed above to illustrate the invention are amenable to easily recognized other like embodiments and variations, and it is intended that these like embodiments and variations be embraced by the spirit and scope of the annexed claims.

TABLE I

| Test No. | Example | Filter Diameter (inches) | Flow Rate (ml/min) | Number of "A"[3] Layers | Volume of PRBC[4] (ml) | WBC[1] (cell/microliter) | Depletion (%) | WBC[2] (cell/microliter) |
|---|---|---|---|---|---|---|---|---|
| 1 | 1 | 2.5 | 15 | 1 | 186 | 5700 | 88 | 677 |
| 2 | 2 | 2.5 | 15 | 1 | 171 | 5700 | 95 | 261 |
| 3 | 1 | 2.5 | 10.5 | 1 | 185 | 7700 | 64 | 2800 |
| 4 | 2 | 2.5 | 6.2 | 1 | 184 | 7700 | 99.8 | 17 |
| 5 | 1 | 2.5 | 10 | 2 | 182 | 6800 | 76.5 | 1600 |
| 6 | 2 | 2.5 | 12 | 2 | 260 | 6800 | 92.6 | 500 |
| 7 | 1 | 2.5 | 7.7 | 3 | 348 | 6100 | 91.7 | 505 |
| 8 | 2 | 2.5 | 2.8 | 3 | 343 | 6100 | >99.99[5] | <5.5[6] |
| 9 | 1 | 3.75 | 12 | 3 | 375 | 7300 | 99.32 | 200 |
| 10 | 2 | 3.75 | 12 | 3 | 369 | 7300 | >99.99[5] | <5.5[6] |

[1]Pre-leucodepletion
[2]Post-leucodepletion
[3]"A" = Layers of filter material, not including prefilter
[4]PRBC = Packed red blood cells
[5]Greater than 99.99%
[6]Less than 5.5 cell/microliter

TABLE II

| Test No. | Example | Filter Diameter (inches) | Flow Rate (ml/min) | Number of "A"[9] Layers | Volume of PRBC[10] (ml) | WBC[7] (cell/microliter) | Depletion (%) | WBC[8] (cell/microliter) |
|---|---|---|---|---|---|---|---|---|
| 11 | 1 | 3.75 | 14 | 2 | 337 | 10800 | 98.61 | 150 |
| 12 | 2 | 3.75 | 13 | 2 | 347 | 10800 | >99.99[11] | <5.5[12] |
| 13 | 3 | 3.75 | 14 | 2 | 354 | 10800 | 99.69 | 33.3 |

[7]Pre-leucodepletion
[8]Post-leucodepletion
[9]"A" = Layers of filter material, not including prefilter
[10]PRBC = Packed red blood cells
[11]Greater than 99.99%
[12]Less than 5.5 cell/microliter

What is claimed is:

1. A filter material for filtering leucocytes from a fraction of or whole blood, comprising:

a shape-sustaining laid web having a thickness of at least about 1 millimeter and a bulk density of between about 0.05 and 0.4 g/cm$^3$ said web having:

(i) a plurality of interlocked, matrix fibers substantially uniformly distributed in said web so as to form a matrix of the fibers with spaces between adjacent interstices of interlocked fibers and the matrix fibers containing at least 75% by weight of the web of glass matrix fibers having an average diameter of between about 1.0 and about 3 microns;

(ii) a plurality of fibrillated particles of polymeric material having fibrils and a surface area of at least about 5 square meters per gram substantially disposed within said spaces and the weight ratio of the fibrillated particles to matrix fibers is between about 1:99 and 40:60; and (iii) a thermoplastic binder disposed at least at crossover positions of said matrix fibers, the amount of the binder being about 0.1% to 10% by weight of the web.

2. The filter material of claim 1 wherein said diameter of the glass matrix fibers is between about 1.0 and about 2.5 microns.

3. The filter material of claim 2 wherein said diameter of the glass matrix fibers is about 1.8 microns.

4. The filter material of claim 1 wherein the average length of the glass fibers is between about 0.3 to 6.0 millimeters.

5. The filter material of claim 4 wherein the matrix fibers contain at least 85% by weight of the web of glass matrix fibers.

6. The filter material of claim 1 wherein the binder has a softening temperature of below about 400° F.

7. The filter material of claim 6 wherein the binder is emulsifiable and is applied to the web as an emulsion.

8. The filter material of claim 1 wherein the add-ons of binder solids is about 1% to 10%.

9. The filter material of claim 8 wherein the add-ons of binder solids is about 5% to 10%.

10. The filter material of claim 1 wherein the binder is flexible at room temperature and has a glass transition temperature above 100° F.

11. The filter material of claim 1 wherein the binder is selected from polyacrylics and acrylates and mixtures thereof.

12. The filter material of claim 1 wherein the matrix fibers are so interlocked together and the fibrillated particles are so interlocked to the matrix fibers that said filter material can withstand a filtering blood pressure drop of at least 2 feet of head without substantial displacement of the fibrillated particles from the web.

13. The filter material of claim 1 wherein at least a portion of the matrix fibers are sheath/core fibers having a sheath of low melt temperature polymer and a core of higher melt temperature polymer and the web has experienced a temperature sufficient to at least soften said low melt polymer and cause at least some adherence of the matrix fibers and to the fibrils of the fibrillated particles.

14. The filter material of claim 13 wherein from about 1% to about 20% of the weight of the web is the sheath/core fibers.

15. The filter material of claim 14 wherein from about 5% to about 20% of the weight of the web is the sheath/core fibers and the filter material can withstand a filtering blood pressure drop of at least 5 feet of head without substantial displacement of the fibrillated particles from the web.

16. The filter material of claim 1 wherein the fibrillated particles are particles of a textile fiber material selected from the group consisting of polyester fiber material, acrylic textile material, nylon fiber material, polyolefin fiber material and cellulosic fiber material.

17. The filter material of claim 16 wherein the textile fiber material of the fibrillated particles is predominantly cellulosic fiber material.

18. The filter material of claim 17 wherein the cellulosic fiber material is cellulose acetate.

19. The filter material of claim 1 wherein the fibrillated particles have lengths of less than about 1000 microns and widths of about 0.1 to 50 microns.

20. The filter material of claim 1 wherein said surface area of the fibrillated particles is at least 10 square meters per gram and up to 100 square meters per gram and the surface area of the filter material is at least 1.5 square meters per gram.

* * * * *